United States Patent [19]

Bush et al.

[11] Patent Number: 5,127,421
[45] Date of Patent: Jul. 7, 1992

[54] IMPLANTATION OF LEADS

[75] Inventors: Mary E. Bush, Fremont; Thomas A. Howell, Palo Alto, both of Calif.

[73] Assignee: Ventritex, Inc., Sunnyvale, Calif.

[21] Appl. No.: 641,500

[22] Filed: Jan. 15, 1991

[51] Int. Cl.⁵ ............................................. A61N 1/05
[52] U.S. Cl. ............................. 128/785; 128/419 P
[58] Field of Search ............ 128/783, 784, 785, 419 P, 128/419 D; 606/129

[56] References Cited

U.S. PATENT DOCUMENTS

| | | | |
|---|---|---|---|
| 3,171,132 | 3/1965 | Dritz . | |
| 3,250,450 | 5/1966 | Le Page et al. . | |
| 3,999,555 | 12/1976 | Person | 128/419 P |
| 4,270,549 | 6/1981 | Heilman | 128/784 |
| 4,548,203 | 10/1985 | Tacker, Jr. et al. | 128/419 D |
| 4,821,723 | 4/1989 | Baker, Jr. et al. | 128/419 D |
| 4,865,037 | 9/1989 | Chin et al. | 128/419 D |
| 4,884,567 | 12/1989 | Elliott et al. | 128/419 D |
| 4,938,231 | 7/1990 | Milijasevic et al. | 128/784 |
| 4,946,457 | 8/1990 | Elliott | 128/419 D |

OTHER PUBLICATIONS

Brochure by the Dritz Corporation—one page.
Article by Dixon et al. from Laboratory Investigation—Defibrillation, vol. 76, No. 5, Nov., 1987, pp. 1176-1184, Entitled: Improved Defibrillation Thresholds with Large Contoured Epicardial Electrodes and Biphasic Waveforms.

Primary Examiner—William E. Kamm
Assistant Examiner—Scott M. Getzow
Attorney, Agent, or Firm—Gerstman & Ellis, Ltd.

[57] ABSTRACT

An electrode on a lead may be implanted at the heart by placing the lead through a hole in the parietal pericardium and positioning the distal end of the lead in a desired position relative to the heart. Thereafter one secures the lead in the desired position by attachment thereof to a fastener member, including the step of attaching the fastener member to the parietal pericardium by compressive action between a pair of opposed jaws of an attachment tool, with one of the jaws being positioned within and the other of the jaws positioned outside of the parietal pericardium. Also, a tool is disclosed for securing leads to a tissue site, particularly in accordance with the above method.

27 Claims, 4 Drawing Sheets

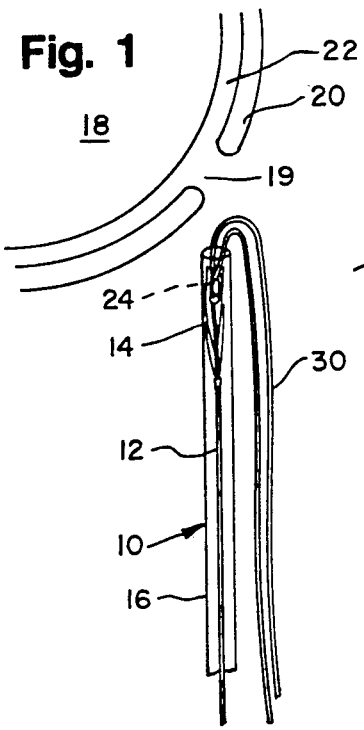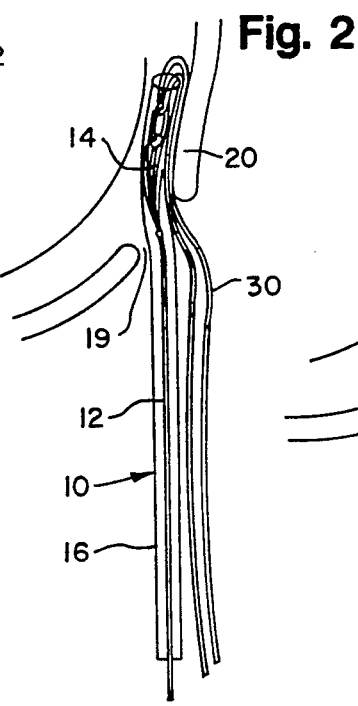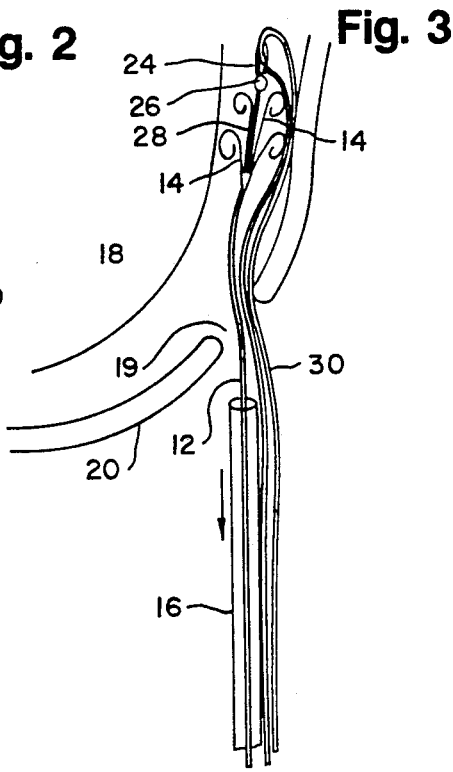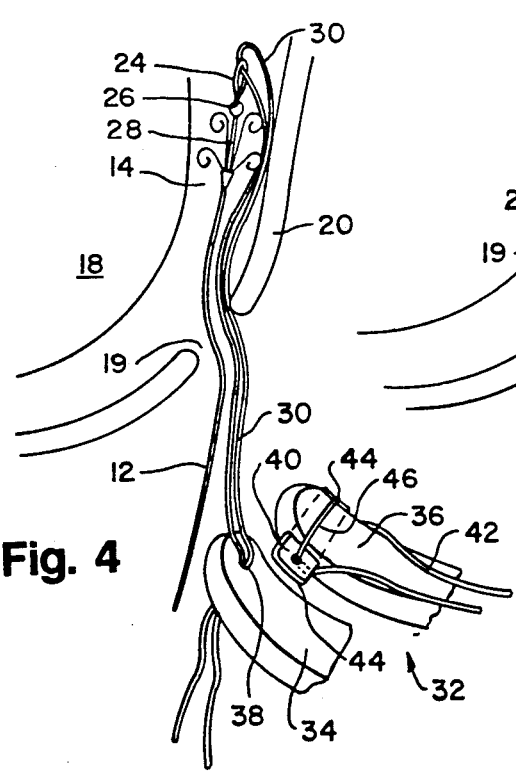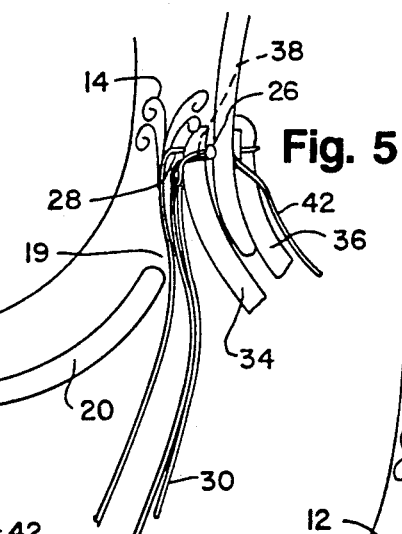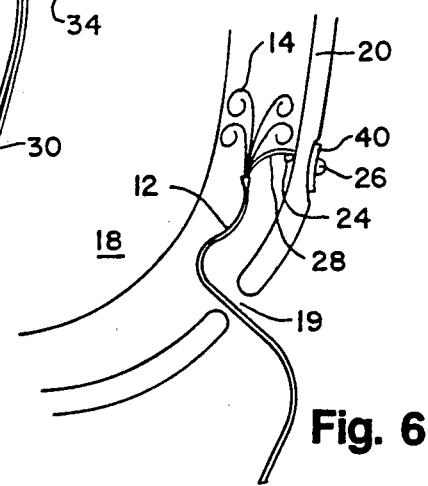

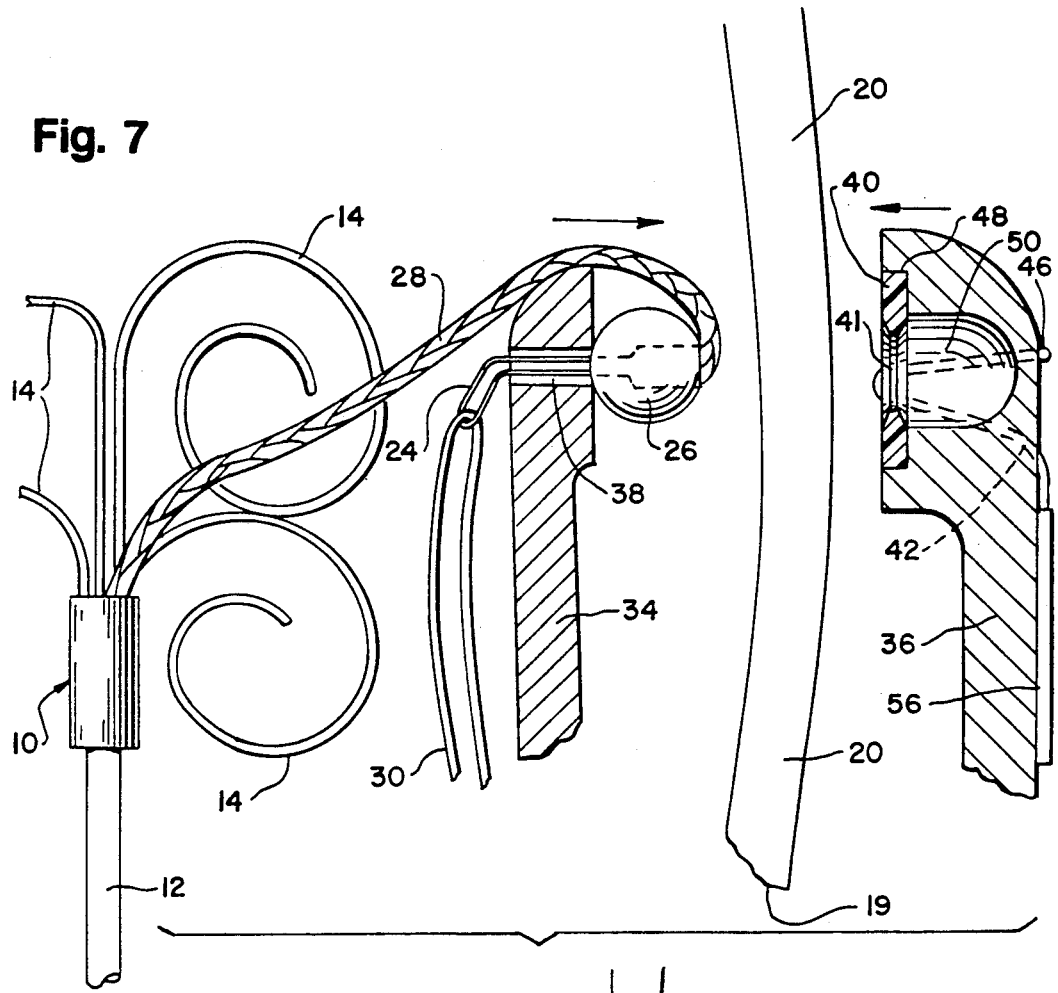

Fig. 9
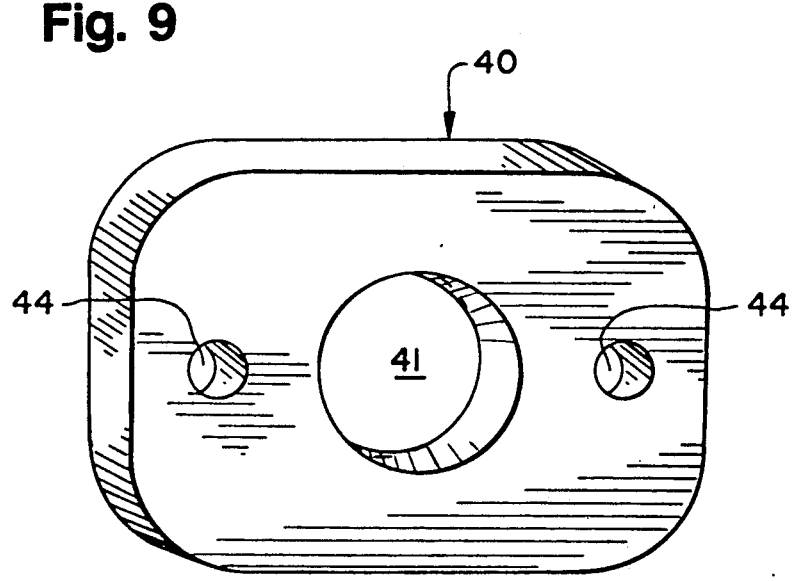
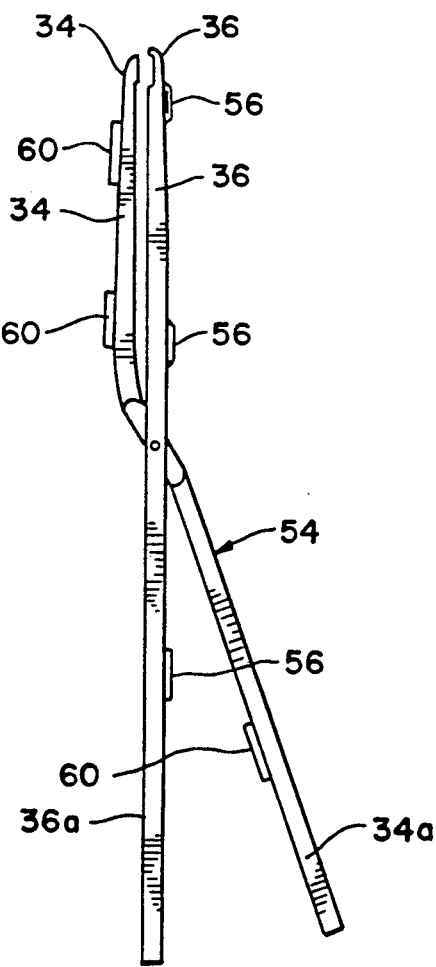
Fig. 10
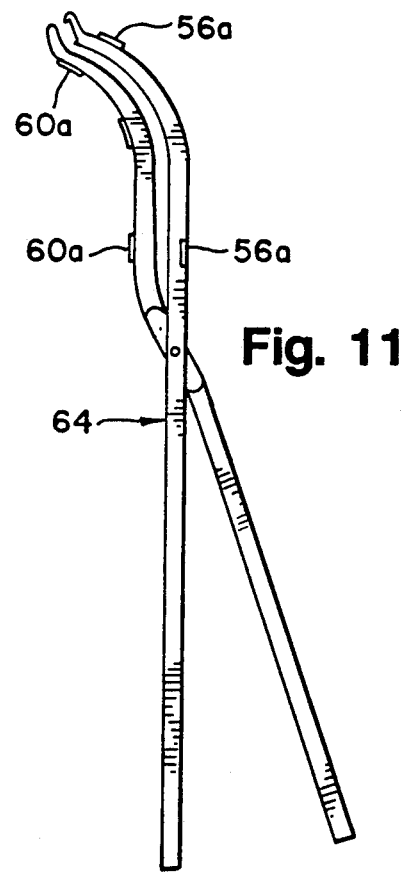
Fig. 11

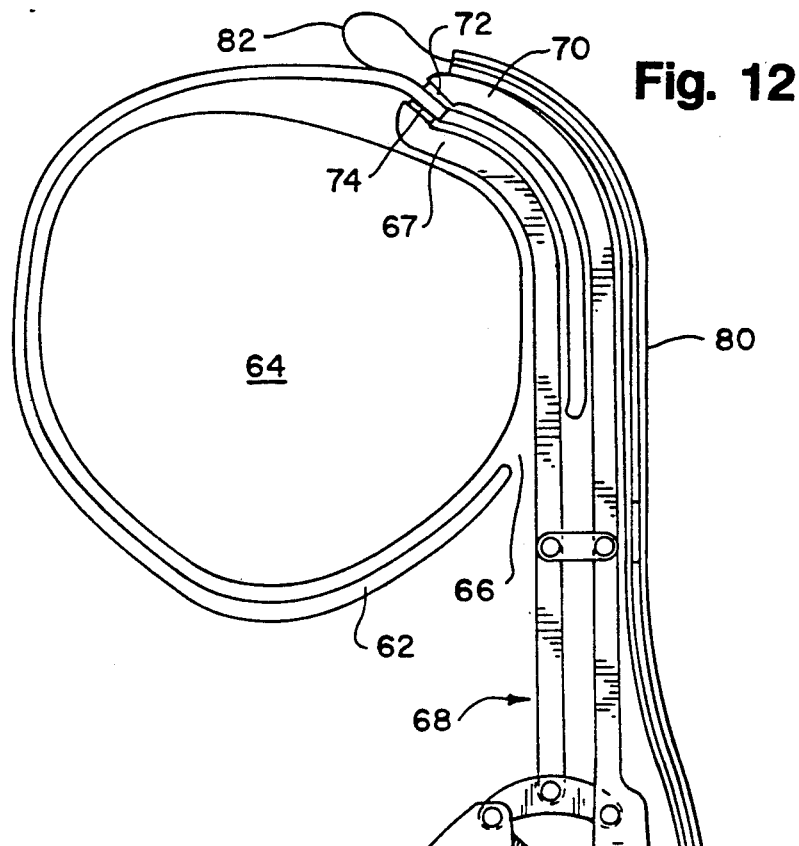
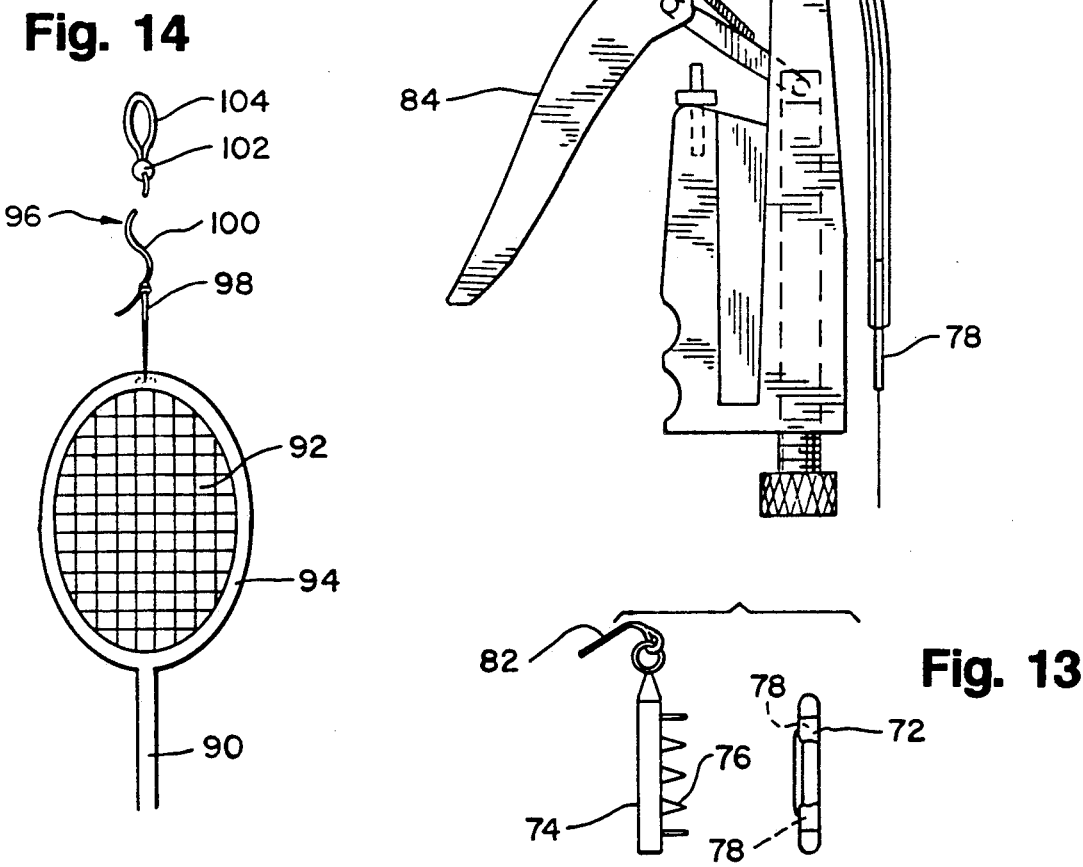
Fig. 12
Fig. 14
Fig. 13

IMPLANTATION OF LEADS

BACKGROUND OF THE INVENTION

This invention relates to a method and apparatus for permanently implanting leads adjacent the heart, plus fixation devices for holding implanted leads in desired positions anywhere in the body.

It is well-known in the field of cardiology that ventricular fibrillation can be effectively treated by the application of electrical shocks to the heart. Such defibrillation may be achieved by the application of electrical paddles to the chest of the patient or directly to the heart tissue, if the chest is open during surgery.

More recent improvements have lead to the development of implantable defibrillators, which monitor the heart for arrhythmias and automatically initiate defibrillation when fibrillation occurs. Such devices often incorporate electrodes that are located on the epicardium or parietal pericardium, being connected to a defibrillation unit by means of a lead.

However, major surgery is generally necessary to implant and affix present defibrillator lead systems into their desired position. For example, a median sternotomy or lateral thoracotomy may be required. Such procedures can be very traumatic to the patient, and may have adverse side effects such as surgical complications, morbidity, or even mortality. Candidates for such a procedure thus may include only those persons for whom the potential benefits outweigh the significant risks. Because of the significant surgical risks of the present lead systems, many patients who might otherwise benefit from the use of an implantable defibrillator are excluded.

The issue of fixation of the lead into a desired position can be important for any implantable device, but it is especially important for defibrillator leads, since the electrodes of the typical pair of defibrillator leads present cannot be allowed to touch each other. When implanting paddle electrodes via sternotomy or thoracotomy, there is adequate access of the leads and surrounding tissues to suture the edges of the leads to those tissues to fixate the leads in place. However, in the case of a deployable lead that has been placed through a small incision, or a paddle electrode placed through a small incision using a limited surgery technique, suturing by hand is not possible due to the lack of access and the lack of visibility. A deployable lead is a lead that is inserted into its position in a transversely collapsed configuration, with the electrodes being then allowed to expand outwardly into a new, laterally expanded configuration which is typically larger than the incision providing entry of the lead into its desired position.

Another difficulty involved in fixating leads to the epicardium, when compared to fixating leads to the endocardium, relates to the lack of trabeculae for engagement with tines, and also the presence of coronary blood vessels that must be avoided if one attempts to use screws or hooks that penetrate the tissue.

By this invention, a lead is preferably attached to the parietal pericardium, and not the epicardium. Thus there is practically no possibility of rupturing coronary vessels or of tearing myocardium. Also, no internal "scope", rigid or flexible, is required in order to provide good fixation of the lead to the parietal pericardium. It is possible to crimp a fixation device as described herein so that no sharp edges of the device are exposed to tissue. Likewise, the fixation device may be visible on x-ray and fluoroscopy, for effective observation both during implantation and afterward. Likewise, fixation devices as described herein may be attached firmly, yet relatively atraumatically, since only fibrous tissue is penetrated and gripped. Thus there is essentially no possibility of puncturing the pleura, and the pericardium remains intact.

The lead may be removed by coring the parietal pericardium, or the lead may be removed by snapping its fixation device apart, while the lead is held by snapping the fixation device together. Also, the fixation device for the lead can be made so unobtrusive that an abandoned fastener can be left attached to the parietal pericardium and a new one emplaced, if desired.

Thus, the invention of this application exhibits significant advantages over prior art methods for implanting leads, particularly adjacent the heart, as shown for example in Chin et al. U.S. Pat. No. 4,865,037 or person U.S. Pat. No. 3,999,555.

DESCRIPTION OF THE INVENTION

In accordance with this invention a method is provided for implanting a lead at the heart, which comprises the following steps:

One places a lead through a hole in the parietal pericardium surrounding the pericardial cavity, and one positions the distal end of the lead in a desired position relative to the heart. Thereafter, one secures the lead in the desired position by attachment of the lead to a fastener member, plus the step of attaching the fastener member to the parietal pericardium, by compressive action between a pair of opposed jaws of an attachment tool, with one of the jaws being positioned within, and the other of said jaws being positioned outside of, the pericardial cavity with the parietal pericardium positioned between said jaws.

The step of attaching a lead to a fastener member may take place during manufacture or before the surgical procedure begins, or at the time of the surgical procedure.

The lead used in the method of this invention may be of essentially collapsed outer diameter while placed through the hole in the parietal pericardium. Then, after such placement, portions of the lead may be laterally deployed outwardly within the pericardial cavity. Examples of such outwardly deployable leads are well known and of various types. The essentially collapsed outer diameter may be provided in conventional manner by a stylet within the electrode, holding it straight, or by a sleeve outside of the electrode to also hold it straight, until the stylet or sleeve are removed, at which time the electrode assumes a new configuration having an enlarged lateral dimension, as shown, for example in the cited Chin et al. U.S. Pat. No. 4,865,037 and other prior art.

Preferably, the above-described fastener member may comprise a pair of engaging parts. Each of the engaging parts may be carried by a separate jaw of the attachment tool described above, until they are attached together by the compressive action provided by the attachment tool.

Specifically, one of the engaging parts of the fastener member may define a bead which is attached to the lead by a flexible member such as a suture filament or the like. The other of the engaging parts defines a plate having a first aperture. The first aperture is sized to allow the bead to be pressed through the aperture in snap-fit relation by the compressive action between the opposed jaws. As specifically discussed below, the bead is pressed through the parietal pericardium, or at least it stretches the parietal pericardium outwardly to a substantial degree, as the aperture of the plate and bead are distorted to receive the bead in a snap-fit relation, so that the bead is trapped in snap-fit relation on the side of the plate opposed to the plate side that faces the majority of the parietal pericardium. Thus, since the plate cannot be pulled through any aperture that is formed in the parietal pericardium by this process, the bead cannot be withdrawn either. Since the bead is attached to the lead by a flexible member, the lead is thus secured to the parietal pericardium.

Preferably, the plate further defines a pair of second apertures which are preferably positioned on opposed edges of the plate with the first aperture being positioned between the second apertures. A first cord extends through the second apertures and secures the plate to one of the jaws of the attachment tool in a position to permit receiving of the bead through the aperture. The first cord is typically a piece of suture material, single strand or multiple strand as may be desired. Thus, particularly when the first cord is arranged with respect to the plate and the one of said jaws as disclosed herein, the first cord may then be removed by pulling one end thereof after the bead has passed through the first aperture, so that the plate is no longer attached to the one jaw. This permits the attachment tool to be removed, leaving the plate behind in its position of attachment with both the parietal pericardium and the lead.

Also, the lead may carry an attachment loop adjacent its distal end. A second cord may extend through the loop and also through an aperture associated with one of the jaws, generally the other of the jaws from the jaw that carries the plate. One then slides the jaw which has the associated aperture along the second cord, after positioning the distal end of the lead in the desired position, to place such jaw in a position for application of the compressive action discussed above to attach the fastener member to the parietal pericardium.

The second cord may be a suture substantially identical to the suture of the first cord. After the fastener member has been attached to the parietal pericardium, the second cord may also be removed by pulling one end thereof, and the attachment tool may then be withdrawn.

Typically, the attachment loop may be carried by the bead discussed above, which bead may be attached to the lead by a flexible member. However, the attachment loop may be attached to the lead in any desired manner and may be used in conjunction with any type of fastener member.

The tool used in accordance with this invention for securing leads to a tissue site may comprise a pair of opposed, movable jaws for applying compressive action to join together first and second attachment means which are each respectively and releasably carried on one of the jaws in opposed relation. Such a tool may be generally conventionally manufactured to accomplish this purpose, except as otherwise described herein.

Preferably the first and second attachment means are of the interlocking variety so that they may be brought together by the jaws, with a body organ portion such as the parietal pericardium positioned between them, for releasable or permanent interlocking engagement. One of the first and second attachment means may then be attached to a lead, so that the lead is secured to the body organ by this action.

Preferably, the first attachment means may comprise a bead of the type described above, while the second attachment means comprises the above-described plate having its first aperture. As stated before, the first aperture is sized to allow the bead to be pressed through the aperture in snap-fit relation by the compressive action between the opposed jaws.

The plate is preferably made of a semi-flexible material having a desired amount of resilience, so that the snap-fit relation may be achieved with relative ease, yet the retention will be strong enough for the desired purposes. The attachment tool of this invention may be so constructed that the first cord as described above extends through tunnel means carried on a first attachment tool arm, which arm also carries the one jaw that carries the plate, to position and house a portion of the first cord and to keep it tight and out of the way. Nevertheless, it remains possible to remove the entire first cord from its engagement holding the plate or other connector onto the one jaw by pulling one end thereof.

Likewise, the other cord may extend through optional tunnel means carried on a second attachment tool arm that also carries the other jaw, to position and house a portion of the other cord. This other cord may also be easily removed out of engagement with the loop as described above to disconnect the second attachment tool arm from the lead, when that is desired.

Thus, the respective cords carried on the attachment tool arms are kept in closely associated relation with the tool arms during the procedure described herein, but they are still readily removable when that is desired.

DESCRIPTION OF THE DRAWINGS

FIGS. 1 through 6 are schematic views of various sequential steps in the method of implanting and affixing a defibrillation electrode lead into the pericardial cavity by attachment to the parietal pericardium;

FIG. 7 is a detailed, elevational view, taken partly schematically, illustrating substantially the step of FIG. 5 in greater detail;

FIG. 8 shows details of a step subsequent to the step of FIG. 7;

FIG. 9 is an enlarged, perspective view of the plate which may serve as one of the engaging parts of the fastener member used in this invention;

FIGS. 10 and 11 are plan views of various designs of attachment tools which may be used in accordance with this invention;

FIG. 12 illustrates another embodiment of the implantation of a lead in accordance with this invention, in which the lead is positioned outside of the parietal pericardium and is secured thereto;

FIG. 13 provides a detailed view of the engaging parts of the fastener member used in FIG. 12; and FIG. 14 is a plan view showing how an attachment loop and fastener may be attached to a lead, particularly a paddle electrode, for use in accordance with this invention.

DESCRIPTION OF SPECIFIC EMBODIMENTS

Referring to the drawings, FIGS. 1 through 6 disclose various steps in the method of implanting a lead at the heart, with FIGS. 7 and 8 showing details of the process. As shown in FIG. 1, a lead 10 comprises a lead body 12 having outwardly deployable electrodes 14, which may be made of conductive metal. Lead body 12 and electrodes 14 are initially closed in an outer sheath 16, typically in a manner as disclosed in Bush et al. U.S. application Ser. No. 591,389, filed Oct. 1, 1990 and entitled Multiple Electrode Deployable Lead. Otherwise, any lead having outwardly deployable electrodes may be used in this particular embodiment, with the electrodes being held in essentially radially collapsed configuration either by a sleeve or by one or more stylets.

Heart 18 of a patient is exposed by a surgical procedure, and an aperture is formed in the parietal pericardium 20, so that access to the pericardial cavity 22 is provided to lead lo.

As one modification to customary deployable electrode leads of the prior art, lead 12 used herein carries a distally mounted loop 24 made of nylon suture material or the like. A magnified view of the distal end of lead 10 is shown in FIG. 7. There, loop 24 is shown being connected to a bead 26 which may be made of plastic, ceramic or metal, and which comprises one of the engaging parts of the fastening member used in this particular embodiment, as previously described. Bead 26 is connected to the distal end of lead 10 by a flexible member 28, typically a piece of multistrand cord or the like for permanent securance of bead 26 to the distal end of lead 12. Also in FIG. 7, electrodes 14 are shown in their outwardly deployed configuration after removal of sheath 16, particularly as shown in FIG. 3.

A cord 30 is provided, extending along the length of lead 10 and passing through loop 24, with the cord then extending rearwardly again along the length of lead 10. Typically, cord 30 is more than double the length of lead 10 so that both of its rear ends extend out of the incision site and the skin during the surgical procedure.

After the aperture 19 has been made in the parietal pericardium 20, the sheathed lead 10, and cord 30 are advanced through such aperture as shown in FIG. 2, until the electrodes 14 of the lead are positioned in the desired spot.

After such positioning takes place, as shown in FIG. 3, sheath or sleeve 16 may be withdrawn. This allows spring electrodes 14 to deploy outwardly as shown.

After removal of sheath 16, as shown in FIG. 4 an attachment tool 32, having opposed jaws 34, 36, is brought to bear, first by threading at least one or preferably both of the lengths of cord 30 through an aperture 38 in jaw 34 of the attachment tool.

It can also be seen that the other jaw 36 of the attachment tool carries a plate 40, which plate is held in position on jaw 36 by cord 42 which extends typically the distance of attachment tool 32, so that the proximal ends of cord 42 and also well outside of the surgical incision used to gain access to the heart area.

The shape of plate 40 is more clearly shown in FIG. 9, in which plate 40 comprises a central first aperture 41 and a pair of side apertures 44. Cord 42 is shown to extend along the length of jaw 36, then passing underneath plate 40 to project upwardly through one of the side apertures 44. A length 46 of the cord 42 then extends transversely across the side of jaw 36 that is opposed to the side that carries plate 40 in a jaw recess 48 (FIG. 7). The cord 42 then passes downwardly through the other side aperture 44 and then extends rearwardly again along the jaw 36. Thus, plate 40 is temporarily retained in position as long as cord 42 is held under tension.

Referring to FIGS. 4 and 5, jaw 34 of the attachment tool is then passed into aperture 19, being guided by the passage of cord 30 through aperture 38 in jaw 34. Eventually, as shown in FIGS. 5, and 7 loop 24 extends through aperture 38, with flexible member 28 extending around the side or end of jaw 34 and bead 26 being seated on aperture 38. Jaws 34, 36 of attachment tool 32 are positioned adjacent an intact portion of the parietal pericardium, spaced from aperture 19 as shown in FIGS. 5 and 7. Plate 40 is shown in FIG. 7 in section, with first aperture 41 being seen in section. A chamber 50 is provided in jaw 36 behind plate 40 and aperture 41.

Then, upon closing of jaws 34, 36, bead 26 may be pressed through aperture 41 in snap-fit relation, with bead 26 fitting into chamber 50, and taking a section of flexible member 28 along with it. Plate 40 is flexible enough, and aperture 41 is sized, to allow this to take place.

Then, each of cords 30 and 42 are pulled at one distal end to cause the entire cord to be withdrawn from the area of jaws 34, 36 and the attachment tool 32. The attachment tool itself may then be withdrawn from the site, leaving the attached lead 12 in a configuration as shown in FIGS. 6 and 8. Bead 26 is shown to be retained on the side of the parietal pericardium 20 remote from that side facing lead 10 by its snap-fit relation with plate 40. Plate 40 is too large to penetrate through the parietal pericardium 20, even should the stretched portion thereof 52 surrounding bead 26 be broken or necrose.

Thus, flexible member 28 is securely anchored to provide secure anchoring to lead 10. Because of this, outwardly deployed electrodes 14 cannot migrate in an undesirable manner, so that a second lead may be positioned at a different but relatively close area of the heart, with good reliance that the respective electrodes of the two leads will never touch.

As an advantage of the method of this invention, before affixation of the lead, it is possible to move the lead around to test defibrillation thresholds until a desirable defibrillation threshold is obtained. Only then, if desired, can the steps illustrated in FIGS. 4 through 8 be performed so that each lead which is implanted in accordance with this invention can be implanted with a high probability of effective performance.

Then, the aperture 19 in parietal pericardium 20 may be sutured together to close the aperture down around lead 10 on all sides.

Thus, a method is provided in which a lead may be implanted at a desired position at the heart without need of visually observing the deployed electrodes 14 and without seeing the exact attachment site of the lead.

FIGS. 10 and 11 show two particular types of attachment tools which may be used in accordance with this invention. The attachment tools may be of the generally conventional design of analogous surgical instruments except for the precise shapes of their jaws, which may be as shown in FIG. 7, and as otherwise indicated in here.

As a specific, different modification, each of the respective jaws 34, 36 of FIG. 10 may carry tunnel means to position and house a portion of the respective cords carried on the jaw and arm of the tool. For example, jaw 36 of tool 54 defines tunnel members 56 through which cord 42 can extend, to hold the cord in a position essentially parallel to the extent of jaw 36 and the corresponding tool arm 36a.

Likewise, jaw 34 may carry one or more tunnel members 60 for the same purpose, positioned along jaw 34 and in its corresponding arm 34a for control and retention of cord 30.

The attachment tool illustrated in FIG. 10 is particularly adapted for emplacing leads at anterior heart positions.

Turning to FIG. 11, a similar emplacement tool is shown which may function in a manner similar to that of the previous disclosure. Specifically, the tool of FIG. 11 is adapted for emplacement of leads at posterior heart positions. Apart from the difference in shape of the tool in FIG. 11, it may function in a manner similar to the tool of FIG. 10. Specifically, tunnel members 56a and 60a may be provided for the retention of the respective cords which are present for purposes described above.

Referring to FIG. 12, an alternate embodiment of attachment tool in accordance with this invention is shown, in the process of attaching a lead with a different retention system.

As before, the parietal pericardium 62 of the patient's heart 64 is opened with an aperture 66, so that one jaw 67 of an attachment tool 68 may be inserted. Another jaw 70 is positioned on the outside of the parietal pericardium, and each of the jaws carries an interengaging part 72, 74 of a fastener member.

As specifically shown in FIG. 13, part 74 of the fastener member may comprise a ring which defines a plurality of prongs 76, while part 72 of the fastener member defines another ring with a facing annular groove 78. To make connection, the prongs of ring 77 fit into the groove 78 of ring 79, and are retained there, in the manner rather of the assembly of a clothing snap on a piece of cloth, with the design being similar to such a conventional clothing snap.

As shown in FIG. 12, lead 78 is carried in a sleeve 80, which may be withdrawn to cause the electrodes at the distal end of lead 78 to expand outwardly in the conventional manner of a deployable lead having one or more electrodes. The distal end of lead 78 is connected to one end of a flexible member 82 such as a strong, permanent surgical suture or the like, while the other end of flexible member 82 is connected to fastener half 72.

Thus, the structure as illustrated in FIGS. 12 and 13 is analogous to the previous embodiment, except that lead 78 is being emplaced outside of the parietal pericardium 62 rather than the inside thereof. When the two jaws are brought together by handle mechanism 84, with the parietal pericardium between them, the fastener member halves 72, 74 are connected together in a permanent manner, if desired, and lead 78 is thus permanently attached in a desired position relative to the heart.

Sleeve 80 is withdrawn to deploy the electrodes of the lead, and tool 68 is correspondingly withdrawn, leaving lead 78 behind. Aperture 66 in the parietal pericardium is sutured, and the patient is closed up.

Thus, by this means and also by the previous embodiment, it is possible to implant one or more leads at a position about the heart or elsewhere, remote from the site of the surgery, well beyond where suturing can take place. Significant advantages of the method of implantation described above may also be achieved by this embodiment of the invention as well as by the previous embodiment.

Turning to FIG. 14, the distal end of a lead 90 is shown, terminating in a conventional paddle electrode 92 formed of a mesh of conductive wires and surrounded by a supporting cuff 94 which contains a suturable fabric, rubber, or the like.

In accordance with this invention, a member 96 is provided for securing an attachment loop and a fastener onto a lead. Member 96 may be used with respect to paddle electrode lead 90 or a deployable lead as disclosed in this application, or any other appropriate type of lead.

Member 96 carries a needle 98 which may be used for suturing. A suture 100 or equivalent cord is connected to the end of the needle, and is of sufficient length to permit suturing or attachment thereof by means of needle 98 to cuff 94, or to any other appropriate spot on typically the distal end of a deployable or other type of lead.

At the end of cord 100 opposed to needle 98, an attachment bead 102 is provided, or any other desired attachment member. Attachment bead 102 may be used in the manner previously described with respect to attachment bead 26.

Then, cord loop 104 is also provided, which cord loop is intended for use in the manner of loop 24 as previously discussed.

Accordingly, by this invention, an attachment bead 102 and a cord loop 104 may be attached to a large variety of leads by simple sewing action, making use of cord 100 and needle 98. Then, when cord 100 has been firmly attached to the lead, needle 98 may be cut away, to prepare any desired lead for use in accordance with this invention.

The above has been offered for illustrative purposes only and is not intended to limit the scope of the invention of this application, which is as defined in the claims below.

That which is claimed is:

1. The method of implanting a lead at the heart, which comprises:
   placing a lead through a hole in the parietal pericardium surrounding the pericardial cavity; positioning the distal end of said lead in a desired position relative to the heart; and thereafter securing said lead in said desired position by attachment of said lead to a fastener member and including the step of attaching said fastener member to said parietal pericardium by compressive action between a pair of opposed jaws of an attachment tool, with one of said jaws being positioned within, and the other of said jaws being positioned outside of, said pericardial cavity with the parietal pericardium positioned between said jaws.

2. The method of claim 1 in which said lead is of essentially collapsed outer diameter while placed through said hole in the parietal pericardium, and portions of said lead are then laterally deployed outwardly within said pericardial cavity.

3. The method of claim 1 in which said fastener member comprises a pair of engaging parts, each being carried by a separate jaw of said attachment tool until attached together by said compressive action.

4. The method of claim 3 in which one of said engaging parts defines a first ring which carries projecting prongs from one side thereof, and the other of said engaging parts defines a second ring defining recesses to receive and retain said prongs, one of said rings carrying means for attachment to said lead.

5. The method of claim 3 in which one of said engaging parts defines a bead which is attached to said lead by a flexible member, and the other of said engaging parts defines a plate having a first aperture, said first aperture being sized to allow said bead to be pressed through said aperture in snap-fit relation by said compressive action between said opposed jaws.

6. The method of claim 5 in which said plate further defines a pair of second apertures positioned on opposed sides of said plate with said first aperture being positioned between said second apertures, and a first cord extending through said second apertures and securing said plate to one of said jaws.

7. The method of claim 6 in which, after said bead has passed through the first aperture, said first cord is removed by pulling one end thereof.

8. The method of claim 1 in which said lead carries an attachment loop adjacent the distal end of said lead, and a second cord extends through said loop and also through an aperture associated with one of said jaws, and including the step of sliding said one jaw along said second cord after positioning the distal end of said lead in said desired position, to place said one jaw in a position for application of said compressive action to attach said fastener member to the parietal pericardium.

9. The method of claim 8 including the step of thereafter removing said second cord by pulling one end thereof.

10. The method of claim 8 in which said attachment loop is carried by a bead which, in turn, is attached to said lead by a flexible member.

11. A member for securing an attachment loop and fastener onto a lead, which comprises: a flexible loop, a fastener, a cord which carries said fastener and flexible loop, and a needle carried on one end of the cord to permit sewing attachment of said member to a lead.

12. The member of claim 11 in which said cord is attached adjacent said one end to a lead and said needle is removed.

13. The member of claim 11 in which said fastener is a bead.

14. A tool for securing leads to a tissue site, said tool comprising a pair of opposed, movable jaws for applying compressive action together; and first and second attachment means which are each respectively releasably carried on one of said jaws, said first attachment means comprising a bead, said second attachment means comprising a plate having a first aperture, said first aperture being sized to allow said bead to be pressed through said aperture in snap-fit relation by said compressive action between said opposed jaws, said bead being attached to a lead.

15. The tool of claim 14 in which a flexible loop is associated with said bead, the one of said jaws that carries said bead defining an aperture, and a first cord extending through said loop and also said aperture to assist in positioning the bead in carried relation with the one jaw.

16. The tool of claim 15 in which said plate is releasably carried on the other of said jaws by releasable securance with another cord.

17. The tool of claim 16 in which said plate further defines a pair of second apertures positioned on opposed sides of said plate with said first aperture being positioned between said second apertures, said other cord extending through said second apertures and securing said plate to one of said jaws.

18. The tool of claim 15 in which said first cord extends through tunnel means carried on a first attachment tool arm that also carries said one jaw, to position and house a portion of said first cord.

19. The tool of claim 15 in which said other cord extends through tunnel means carried on a second attachment tool arm that also carries said other jaw, to position and house a portion of said other cord.

20. The method of implanting a lead at the heart, which lead is of essentially collapsed outer diameter in an initial condition, which method comprises:

placing said lead through a hole in the parietal pericardium surrounding the pericardial cavity; positioning the distal end of said lead in a desired position relative to the heart; laterally deploying portions of said lead outwardly within said pericardial cavity; and securing said lead in said desired position by attachment of said lead to a fastener member and attaching a pair of engaging parts that comprise said fastener member to said parietal pericardium by compressive action between a pair of opposed jaws of an attachment tool, with one of the jaws carrying one of said engaging parts and being positioned within said pericardial cavity and the other of said jaws carrying the other of said engaging parts and being positioned outside of said pericardial cavity with the parietal pericardium positioned between said jaws.

21. The method of claim 20 in which one of said engaging parts defines a bead which is attached to said lead by a flexible member, and the other of said engaging parts defines a plate having a first aperture, said first aperture being sized to allow said bead to be pressed through said aperture in snap-fit relation by said compressive action between said opposed jaws.

22. The method of claim 21 in which said plate further defines a pair of second apertures positioned on opposed sides of said plate with said first aperture being positioned between said second apertures, and a first cord extending through said second apertures and securing said plate to one of said jaws.

23. The method of claim 22 in which said lead carries an attachment loop adjacent the distal end of said lead, and a second cord extends through said loop and also through an aperture associated with one of said jaws, including the step of sliding said one jaw along said second cord after positioning the distal end of said lead in said desired position, to place said one jaw in a position for application of said compressive action to attach said fastener member to the parietal pericardium.

24. A tool for securing leads to a tissue site, said tool comprising a pair of opposed, movable jaws for applying compressive action together; and first and second attachment means which are each respectively releasably carried on said jaws, said first and second attachment means being capable of interlocking relation for securance together with body tissue carried between said first and second attachment means whereby said attachment means becomes secured to a tissue site by said compressive action together between said opposed jaws, one of said attachment means being attached to a lead.

25. The tool of claim 24 in which a flexible loop is associated with one of said attachment means, the one of said jaws that carries said one attachment means defining an aperture, and a first cord extending through said loop and also said aperture to assist in positioning said attachment means in carried relation with the one jaw.

26. The tool of claim 25 in which the other of said attachment means is releasably carried on the other of said jaws by releasable securance with another cord.

27. The tool of claim 26 in which said first cord extends through tunnel means carried on a first attachment tool arm that also carries said one jaw, to position and house a portion of said first cord, and said other cord extends through tunnel means carried on a second attachment tool arm that also carries said other jaw, to position and house a portion of said other cord.

* * * * *